(12) United States Patent
Meyer

(10) Patent No.: US 7,097,649 B2
(45) Date of Patent: Aug. 29, 2006

(54) DEVICE FOR INSERTING A LENS INTO AN EYE

(75) Inventor: Rolf Meyer, Port (CH)

(73) Assignees: Anton Meyer & Co. AG, Nidau (CH); Asico LLC, Westmont, IL (US)

( * ) Notice: Subject to any disclaimer, the term of this patent is extended or adjusted under 35 U.S.C. 154(b) by 0 days.

(21) Appl. No.: 10/224,321

(22) Filed: Aug. 21, 2002

(65) Prior Publication Data
US 2003/0040755 A1    Feb. 27, 2003

(30) Foreign Application Priority Data
Aug. 23, 2001    (EP) ................................ 01810823

(51) Int. Cl.
*A61F 9/00* (2006.01)
*A61F 13/20* (2006.01)
*A61M 31/00* (2006.01)

(52) U.S. Cl. ..................................................... 606/107
(58) Field of Classification Search ............... 606/1, 606/107, 166; 604/59–64
See application file for complete search history.

(56) References Cited

U.S. PATENT DOCUMENTS

| | | | |
|---|---|---|---|
| 3,744,493 A * | 7/1973 | Booher et al. ................. 604/62 |
| 4,423,809 A | 1/1984 | Mazzocco |
| 4,516,969 A * | 5/1985 | Kintner ....................... 604/187 |
| 4,573,998 A | 3/1986 | Mazzocco |
| 4,702,244 A | 10/1987 | Mazzocco |
| 4,715,373 A | 12/1987 | Mazzocco et al. |
| 4,834,717 A * | 5/1989 | Haber et al. ................. 604/193 |
| 4,955,889 A * | 9/1990 | Van Gent .................... 606/107 |
| 5,098,439 A * | 3/1992 | Hill et al. ..................... 606/107 |
| 5,354,333 A | 10/1994 | Kammann et al. |
| 5,616,148 A * | 4/1997 | Eagles et al. ................. 606/107 |
| 5,620,453 A * | 4/1997 | Nallakrishnan ............. 606/166 |
| 5,643,276 A | 7/1997 | Zaleski |
| 5,776,191 A | 7/1998 | Mazzocco |
| 5,782,802 A * | 7/1998 | Landau ......................... 604/68 |
| 5,865,795 A * | 2/1999 | Schiff et al. .................. 604/70 |
| 5,902,278 A | 5/1999 | Aguilar ....................... 604/227 |
| 6,048,348 A * | 4/2000 | Chambers et al. .......... 606/107 |
| 6,059,791 A | 5/2000 | Chambers |
| 6,083,202 A * | 7/2000 | Smith ...................... 604/164.01 |
| 6,179,843 B1 * | 1/2001 | Weiler ......................... 606/107 |
| 6,203,549 B1 | 3/2001 | Waldock |
| 6,214,015 B1 * | 4/2001 | Reich et al. ................. 606/107 |
| 6,251,114 B1 * | 6/2001 | Farmer et al. ............... 606/107 |
| 6,607,537 B1 * | 8/2003 | Binder ......................... 606/107 |

FOREIGN PATENT DOCUMENTS

EP    0 477 466 A1    5/1991
WO    WO99/59668    11/1999

* cited by examiner

*Primary Examiner*—Michael J. Hayes
*Assistant Examiner*—Michael G. Mendoza
(74) *Attorney, Agent, or Firm*—Browdy and Neimark, PLLC

(57) ABSTRACT

A device for inserting a lens into an eye has a grip body (1) with a lens holder (13) for holding the lens, and a plunger (2) which can be displaced in the grip body (1) for guided insertion of the lens into the eye. A ball-bearing bush (3) is arranged in the grip body (1), the plunger (2) being mounted so as to be laterally displaceable in this ball-bearing bush (3). This allows the device to be operated using one hand, said device additionally having good slide properties and permitting an at all times guided lateral or rotational movement of the plunger.

15 Claims, 4 Drawing Sheets

DEVICE FOR INSERTING A LENS INTO AN EYE

TECHNICAL FIELD

The invention relates to a device for inserting a lens into an eye.

PRIOR ART

Nowadays, in ophthalmic surgery, opaque natural eye lenses are replaced by artificial lenses. In this procedure, the patient's opaque lens is first removed. The surgeon then introduces the artificial lens into the eye with the aid of two forceps. The first forceps is used to fold the lens, and the second forceps is used to insert the lens. This demands that the surgeon have a very steady hand and considerable practice in guiding the two forceps.

A device called an injector permits a certain degree of guiding when fitting artificial lenses. This device for inserting a lens into an eye consists mainly of a grip body and of a plunger which can be displaced in the grip body via a thread. In the front area of the grip body there is a lens holder into which a lens to be inserted is placed. By rotating the plunger, this lens can then be pushed through a front opening of the lens holder, the lens being folded in the process. By further pushing, the lens is introduced in the folded state into the eye. The thread indeed permits exact guiding of the plunger. However, a disadvantage is that the surgeon needs both hands in order to rotate the plunger. Moreover, it is relatively difficult to hold the injector straight during the rotation.

EP-A-0,477,766 moreover discloses a motor-driven injector. A short push rod for guided insertion of the lens is present in a grip body, the push rod being operatively connected to a manipulator which is likewise arranged in the grip body. The manipulator has a rotary drive mechanism in the form of a direct voltage micromotor. The movement of the motor is transmitted as a linear movement to the push rod via a spindle-nut drive. The push rod is guided in the axial direction in the front area of the grip body via a miniature ball-bearing. However, since the insertion of a lens requires an extremely fine touch, practiced surgeons prefer manually activatable operating instruments.

SUMMARY OF THE INVENTION

It is therefore an object of the invention to make available a device of the type mentioned at the outset for inserting a lens into an eye, which device can be operated manually and using one hand and yet permits exact guiding of the plunger.

According to the invention, the plunger is mounted so as to be longitudinally movable in a ball-bearing bush. In this way, the manual injector can be operated using one hand. To manually displace the plunger, it is necessary, as in the case of a syringe, simply to exert a pressure on the plunger. By means of being mounted in the ball-bearing bush, the plunger has improved slide properties, which in turn permits an even advance movement of the plunger and consequently an even insertion of the lens. The arrangement of the ball-bearing bush in the rear end of the grip body directed away from the lens holder avoids a lever effect in the area of the guide and guarantees optimum weight distribution.

Precise guiding of the plunger is guaranteed by a guide groove which is incorporated in the plunger and into which there engages a guide element arranged in the grip body.

In a first embodiment, the guide groove is of rectilinear design, so that the plunger can be displaced in a guided manner in a straight line.

In a second embodiment, the guide groove has a spiral, so that the plunger can additionally be rotated in a guided manner during displacement. If the spiral is arranged in the rear area of the plunger, this rotation, at the end of the insertion movement, allows the lens to unfold in the eye.

Further advantageous embodiments will become evident from the dependent patent claims.

BRIEF DESCRIPTION OF THE DRAWING

The subject of the invention is explained below with reference to preferred illustrative embodiments which are depicted in the attached drawing, in which.

PREFERRED EMBODIMENTS OF THE INVENTION

Figure 1:
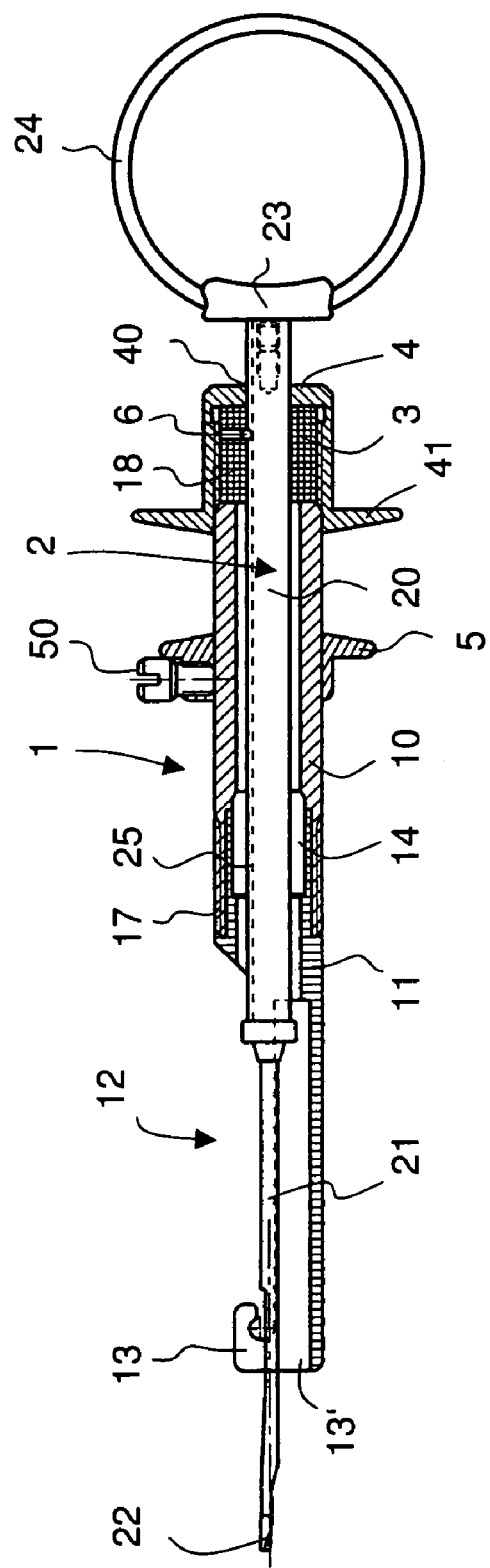
FIG. 1 shows an injector according to the invention in a first embodiment.
Figure 2:
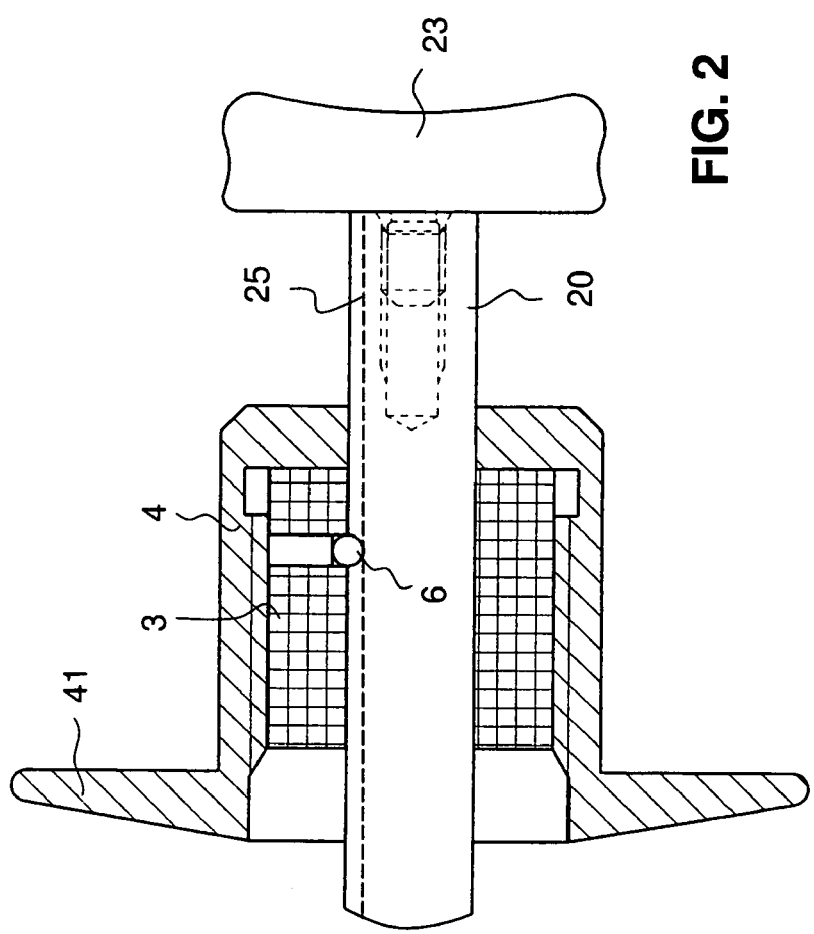
FIG. 2 shows a cutout section from FIG. 1 in an enlarged view.

FIGS. 1 and 2 show an injector according to the invention in a first embodiment. It comprises a grip body 1 in which a plunger 2 is displaceably mounted. Both grip body 1 and plunger 2 are preferably made of metal, in particular titanium.

The grip body 1 has a sleeve 10 which is closed off at its rear end by a closure cap 4. At its front end, the sleeve 10 merges into a grip front part 11. In the example shown here, the grip front part 11 is a separate component which is screwed to the sleeve 10 via a first thread 17.

At its forward end directed away from the sleeve 10, the grip front part 11 has a lens holder 13 for holding an artificial lens. Behind the lens holder 13, the grip front part 11 has an elongate, open insert window 12 through which the lens is fitted into the lens holder 13. At its front end, the lens holder 13 has a through-opening 13' through which the lens is pushed out. As can be seen from FIG. 3, a window 13" can be formed in the lens holder 13 in order to check the position of the fitted lens.

The sleeve 10 preferably has a closed jacket. A ball-bearing bush 3 is arranged in the rear area of the sleeve 10. This ball-bearing bush 3 is enclosed by the closure cap 4, which is screwed onto the sleeve 10 via a second thread 18. In this illustrative embodiment, the ball-bearing bush 3 is fixed in position relative to the sleeve 10. This can be achieved, for example, by the closure cap 4, in contrast to the ball-bearing bush 3, not having a round cross section. In another variant, knobs are arranged on the outer jacket of the ball-bearing bush 3 in order to secure it against turning.

The ball-bearing bush 3 has a defined external diameter. It preferably has metal webs cast into its jacket, protruding from the jacket surface and extending in the longitudinal direction. In this way, the ball-bearing bush 3 can also be made of plastic. The ball-bearing bush 3 preferably has a plurality of ball bearings extending in the longitudinal direction. Four ball-bearing tracks distributed uniformly about the internal circumference have proven expedient, these ball-bearing tracks extending at least approximately along the entire length of the ball-bearing bush 3.

At its front end, the closure cap 4 has a protruding peripheral flange 41 which, as in the case of a syringe, serves as a finger support for the surgeon's fingers, preferably for the index finger and middle finger. At the other end, the closure cap 4 is closed except for a through-opening 40. A second flange 5 is preferably arranged on or integrally formed onto the sleeve 10 and serves as a front limit stop for the surgeon's fingers. If, as is shown here, the second flange 5 is a separate element which can be secured in a releasable manner on the sleeve 10 via a fastening screw 50 and is displaceable along said sleeve 10, then the distance between the first flange and the second flange can be adapted to the thickness of the surgeon's fingers.

The plunger 2 extends through the sleeve 10 and with its rear end protrudes from the through-opening of the closure cap 4. The plunger 2 consists mainly of a rear plunger head 23, a plunger middle part 20, a plunger needle 21 and a plunger tip 22. The plunger needle 21 is preferably connected releasably to the plunger middle part 20, so that a new needle can be used depending on the nature of the lens. In addition, it can also be used as a disposable needle. The plunger tip 22 is arranged on or integrally formed onto the tip of the needle 21. Its shape too varies depending on the nature of the lens.

The plunger head 23 forms the rear end of the plunger 2. It is connected to a finger ring 24. The plunger head 23 serves as a surface for the surgeon's thumb to press on, in order to push the plunger 2 forward laterally in the sleeve 10 using one hand. The finger ring 24 makes it possible to return the plunger 2 using the thumb, without having to change the position of the fingers holding the injector. When the plunger 2 is pushed forward, the artificial lens lying in the lens holder 13 is folded, pushed forward out of the injector and fitted into the eye with precisely proportioned pressure and in a guided direction. In FIG. 1, the injector is shown with the plunger 2 advanced, after insertion of a lens.

The ball bearings of the ball-bearing bush 3 permit low-friction displacement of the plunger. As its guide means, the plunger 2 is provided with a rectilinear guide groove 25 which extends at least along the entire path of displacement of the plunger 2. In the example shown here, it extends along the length of the plunger middle part 20. Arranged in the ball-bearing bush 3 there is a guide element 6, here in the form of a protruding metal ball, upon which pressure is exerted so that it engages in the guide groove 25 and thus prevents turning of the plunger 2 during the advance movement. The guide element 6 can also be arranged outside the ball-bearing bush 3, and in this case at least it is acted upon by a spring. Such a guide element 6 is shown in FIGS. 3 and 4.

In order to prevent a dynamic pressure and consequently an inhibiting counterforce on the plunger 2, the sleeve 10 also has at least one relief chamber 14 in order to relieve the pressure of the air which is compressed when the plunger 2 is pushed forward.

Figure 3:
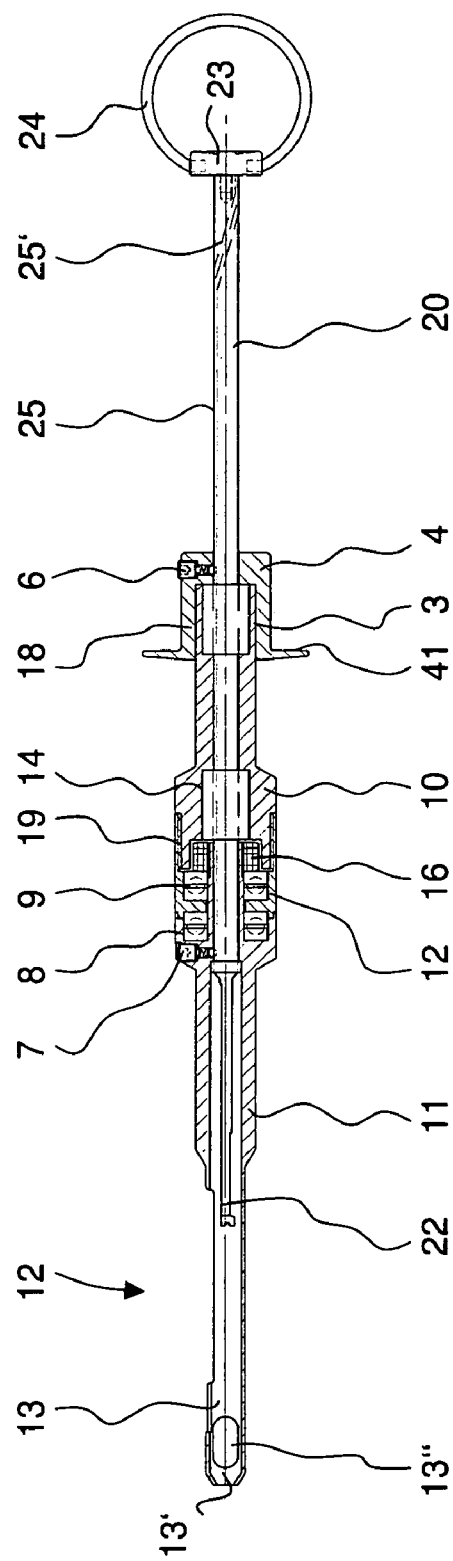
FIG. 3 shows an injector according to the invention in a second embodiment.
Figure 4:
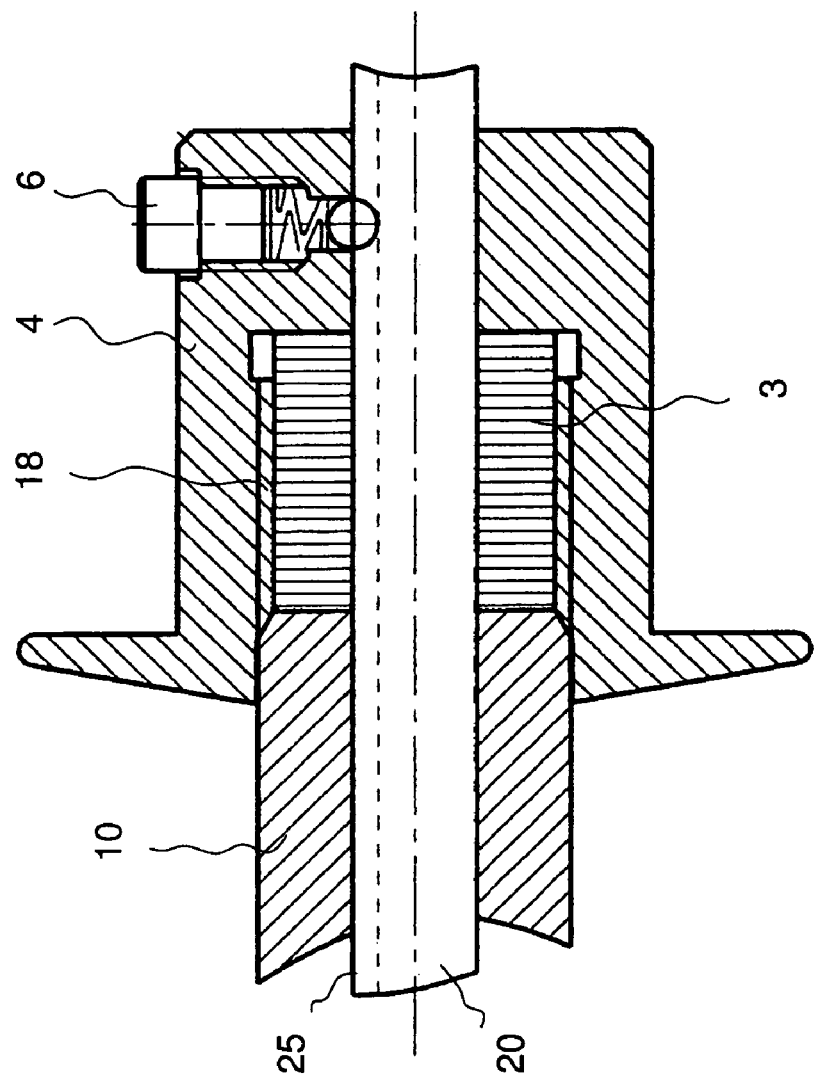
FIG. 4 shows a cutout section from FIG. 3 in an enlarged view.

FIGS. 3 and 4 show a second embodiment of the injector according to the invention. Identical parts are provided with the same reference numbers as in FIGS. 1 and 2, so that these parts will not be dealt with further here. In contrast to the first embodiment, the plunger 2 has a guide groove 25 which is provided at the rear end with a spiral 25'. The guide element 6 again engages in the guide groove 25. If the plunger 2 is now advanced until the groove passes into the spiral 25', the plunger 2 is then rotated in a guided manner. In order to further guarantee the bearing, the ball-bearing bush 3 in this embodiment is not fixed in position, but instead is arranged rotatably on the sleeve 10 so that it rotates together with the plunger 2.

In the embodiment shown here, the grip front part 11 rotates together with the plunger 2. For this purpose, a grip middle part 15 is provided between grip front part 11 and sleeve 10, which grip middle part 15 is connected to the sleeve 10 via a third thread 18. A first axial bearing 8 is arranged between the grip front part 11 and the grip middle part 15, and a second axial bearing 9 is arranged between the grip middle part 15 and sleeve 10. The second axial bearing 9 is in this case held in its position by means of a nut 16.

A carrier 7 is arranged in the grip front part 11. It is of identical construction to the spring-mounted guide element 6 and likewise engages in the guide groove 25 of the plunger 2. If the plunger 2 is now rotated via the spiral 25', the grip front part 11 is also rotated through the connection via the carrier 7. This rotation at the end of the insertion of the lens simplifies the unfolding of the lens and its placement in the eye.

If only the plunger 2 is to be rotated, but not the grip front part 11, then it is also possible to arrange a second spiral on the plunger. The two spirals must then have the same distance as the guide element 6 from the carrier 7. In addition, the length of the plunger 2 is to be dimensioned such that the second spiral comes to lie in front of the first guide element 6 when the plunger 2 is in the extended starting position, that is to say before the start of the advance movement.

The device according to the invention can be operated using one hand, said device additionally having good slide properties and permitting an at all times guided lateral or rotational movement of the plunger.

LIST OF REFERENCE NUMBERS 1 grip body
10 sleeve
11 grip front part
12 insert window
13 lens holder
13' through-opening
13" window
14 relief chamber
15 grip middle part
16 nut
17 first thread
18 second thread
19 third thread
2 plunger
20 plunger middle part
21 plunger needle
22 plunger tip
23 plunger head
24 finger ring
25 guide groove
25' spiral
3 ball-bearing bush
4 closure cap
40 through-opening
41 first flange
5 second flange
50 fastening screw
6 guide element
7 carrier
8 first axial bearing
9 second axial bearing

The invention claimed is:

1. A manually operated device for inserting a lens into an eye, said device comprising:
    a grip body with a lens holder located at a first end of the grip body for holding the lens,
    a plunger with a plunger head serving as a surface for a surgeon's thumb to press on in order to displace the plunger manually in the grip body for guided insertion of the lens into the eye,
    a ball-bearing bush arranged in the grip body, said plunger being mounted so as to be longitudinally movable in said ball-bearing bush, said ball-bearing bush being arranged near a second end of the grip body opposite from the lens holder.

2. The device as claimed in claim 1, wherein the ball-bearing bush is arranged in a fixed position in the grip body.

3. The device as claimed in claim 1, wherein the plunger having a guide groove into which engages a guide element arranged in the grip body, and the guide element is positioned in the ball-bearing bush.

4. The device as claimed in claim 1, further comprising:
    a protruding finger support arranged on the grip body for supporting a surgeon's fingers during use; and
    a front limit stop for the surgeon's fingers arranged on the grip body at a distance spaced from the protruding finger support.

5. The device as claimed in claim 4, wherein the front limit stop in displaceably arranged on the grip body such that a distance between the protruding finger support and the front limit stop may be changed in accordance with a thickness of the surgeon's fingers.

6. A manually operated device for inserting a lens into an eye, said device comprising:
    a grip body with a lens holder located at a first end of the grip body for holding the lens,
    a plunger with a plunger head serving as a surface for a surgeon's thumb to press on in order to displace the plunger manually in the grip body for guided insertion of the lens into the eye,
    a ball-bearing bush arranged near a second end of the grip body opposite from the first end, the plunger being mounted so as to be longitudinally movable in said ball-bearing bush, said plunger having a guide groove into which engages a guide element arranged in the grip body and wherein the device is springless.

7. The device as claimed in claim 6, wherein the guide element is positioned in the ball-bearing bush.

8. The device as claimed in claim 6, wherein the ball-bearing bush is arranged in a fixed position in the grip body.

9. The device as claimed in claim 6, wherein the guide groove is rectilinear.

10. The device as claimed in claim 6, wherein the guide groove has a spiral at least in the rear area of the plunger, so that the plunger can be rotated in a guided manner.

11. The device as claimed in claim 10, wherein the spiral is arranged in the rear area of the plunger.

12. The device as claimed in claim 6, further comprising:
    a protruding finger support arranged on the grip body for supporting a surgeon's fingers; and
    a front limit stop for the surgeon's fingers arranged on the grip body at a distance spaced from the protruding finger support.

13. The device as claimed in claim 12, wherein the front limit stop in displaceably arranged on the grip body such that a distance between the protruding finger support and the front limit stop may be changed in accordance with a thickness of the surgeon's fingers.

14. A device for inserting a lens into an eye, said device having a grip body with a lens holder for holding the lens, and a plunger which can be displaced manually in the grip body for guided insertion of the lens into the eye, wherein a ball-bearing bush is arranged in the grip body, the plunger is mounted so as to be longitudinally movable in this ball-bearing bush, and the plunger has a guide groove into which there engages a guide element arranged in the grip body, wherein the guide groove has a spiral at least in the rear area of the plunger, so that the plunger can be rotated in a guided manner, wherein the grip body has a sleeve and a grip front part connected to the sleeve via axial bearings, and a carrier arranged in the grip front part engages in the guide groove so that the grip front part can be rotated in a guided manner with the plunger.

15. A device for inserting a lens into an eye, said device having a grip body with a lens holder for holding the lens, and a plunger which can be displaced manually in the grip body for guided insertion of the lens into the eye, wherein a ball-bearing bush is arranged in the grip body, the plunger is mounted so as to be longitudinally movable in this ball-bearing bush, and the plunger has a guide groove into which there engages a guide element arranged in the grip body, wherein the guide groove has a spiral at least in the rear area of the plunger, so that the plunger can be rotated in a guided manner, wherein the ball-bearing bush is arranged rotatably in the grip body and can be rotated in a guided manner together with the plunger.

* * * * *